(12) United States Patent
Camps et al.

US009068972B2

(10) Patent No.: US 9,068,972 B2
(45) Date of Patent: Jun. 30, 2015

(54) GFP MUTAGENESIS AMPLIFICATION: USE OF A FLUORESCENCE-ANTIBIOTIC RESISTANCE FUSION DUAL REPORTER CONSTRUCT TO PROVIDE QUANTITATIVE AND HIGHLY SENSITIVE DETECTION OF MUTATIONS

(75) Inventors: Manel Camps, Santa Cruz, CA (US); Jennifer Allen, Santa Cruz, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 278 days.

(21) Appl. No.: 13/504,911

(22) PCT Filed: Nov. 2, 2010

(86) PCT No.: PCT/US2010/055025
§ 371 (c)(1),
(2), (4) Date: Apr. 27, 2012

(87) PCT Pub. No.: WO2011/053944
PCT Pub. Date: May 5, 2011

(65) Prior Publication Data
US 2012/0302461 A1 Nov. 29, 2012

Related U.S. Application Data

(60) Provisional application No. 61/257,080, filed on Nov. 2, 2009, provisional application No. 61/363,296, filed on Jul. 12, 2010.

(51) Int. Cl.
| | | |
|---|---|---|
| G01N 21/64 | (2006.01) | |
| C12N 15/63 | (2006.01) | |
| C40B 30/06 | (2006.01) | |
| G01N 33/50 | (2006.01) | |

(52) U.S. Cl.
CPC ........ G01N 33/5023 (2013.01); G01N 2500/10 (2013.01)

(58) Field of Classification Search
None
See application file for complete search history.

(56) References Cited

U.S. PATENT DOCUMENTS

| 6,638,732 B1 | 10/2003 | Evans | |
|---|---|---|---|
| 6,667,153 B1 * | 12/2003 | Thomas | ...................... 435/6.14 |
| 2009/0068646 A1 | 3/2009 | Bacher et al. | |

FOREIGN PATENT DOCUMENTS

EP 1176211 1/2002

OTHER PUBLICATIONS

Raz et al., "B-Lactamase as a Marker for Gene Expression in Live Zebrafish Embryos", Developmental Biology, vol. 203, p. 290-294 (1998).*
Schmid et al., "Mutagenicity test system based on a reporter gene assay for short-term detection of mutagens (MutaGen assay)", Mutation Research, 535, p. 55-72 (2003).*
Arai et al., "Construction of Green Fluorescent Protein Reporter Genes for Genotoxicity Test (SOS/umu-Test) and Improvement of Mutagen-Sensitivity", Journal of Bioscience and Bioengineering, vol. 92, No. 3, p. 301-304 (2001).*
Pedelacq et al., "Engineering and characterization of a superfolder green fluorescent protein", Nature Biotechnology, vol. 24, No. 1, p. 79-88 + Erratum on p. 1170 (2006).*
Alva Biran et al., Genetically Engineered Bacteria for Genotoxicity Assessment; Hdb Env Chem (2009) 5J: 161-186.
Daniel Krewski et al., Toxicity Testing in the 21st Century; *Journal of Toxicology and Environmental Health*, Part B, 13:51-138, 2010.
Farhana Masood et al., Title of the book "Environmental Protection Strategies for Sustainable Development Strategies for Sustainability"; Editors: Malik, Abdul; Grohmann, Elisabeth; Publisher: Springer Netherlands; 2012, Chapter 7. Methods for Genotoxicity Testing of Environmental Pollutants.
Georg Reifferscheid et al., Cell-Based Genotoxicity Testing; Adv Biochem Engin/Biotechnol (2010) 118: 85-112.
Umbuzeiro et al., Comparison of the *Salmonella*/Microsome Microsuspension Assay with the new Microplate Fluctuation Protocol for Testing the Mutagenicity of Environmental Samples; Environmental and Molecular Mutagenesis 51:31-38 (2010).
Lal et al., Proc nat acad sci YSA Mar. 19 vol. 99 No. 6 pp. 3651-3656, Lai et al., PNAS vol. 99, No. 6, p. 3651-3656 (Mar. 19, 2002).
Umbuzeiro et al., Comparison of the *Salmonella*/Microsome Microsuspension Assay with the new Microplate Fluctuation Protocol for Testing the Mutagenicity of Environmental Samples; Environmental and Molecular Mutagenesis 51;31-38 (2010).

* cited by examiner

*Primary Examiner* — Heather Calamita
*Assistant Examiner* — Jonah Smith
(74) *Attorney, Agent, or Firm* — Adam Warwick Bell; Matthew Rupert Kaser

(57) ABSTRACT

A reversion mutation assay that is unique in providing a quantitative readout for mutagenesis. This assay is based on the creation of a functional GFP-β-lactamase fusion protein as a reporter providing both antibiotic resistance and fluorescence. This dual reporter is placed in a multicopy plasmid to increase the number of targets, with a reversion site at the N-terminus. Rare mutations at the reversion site allow read-through of the fusion protein, producing both beta-lactamase (providing antibiotic resistance) and GFP (emitting fluorescence). In the presence of carbenicillin, beta-lactamase production confers a selective advantage that allows amplification of mutant plasmids, raising the level of fluorescence emitted by GFP to levels that are detectable by fluorimetry. A window of time can be found where fluorescence is proportional to the number of mutation events at the reversion site, making fluorescence a quantitative measure of mutagenesis. Quantitative (as opposed to binary) detection of mutations allows substantial savings in test sample. This has applications in drug discovery, allowing high-throughput screening for DNA-targeting compounds and early pre-screening of leads for potential carcinogenic activity. The increased sensitivity of this assay also facilitates monitoring complex environmental samples.

19 Claims, 14 Drawing Sheets

Fig. 1a comparison between Ames MPF and GAM
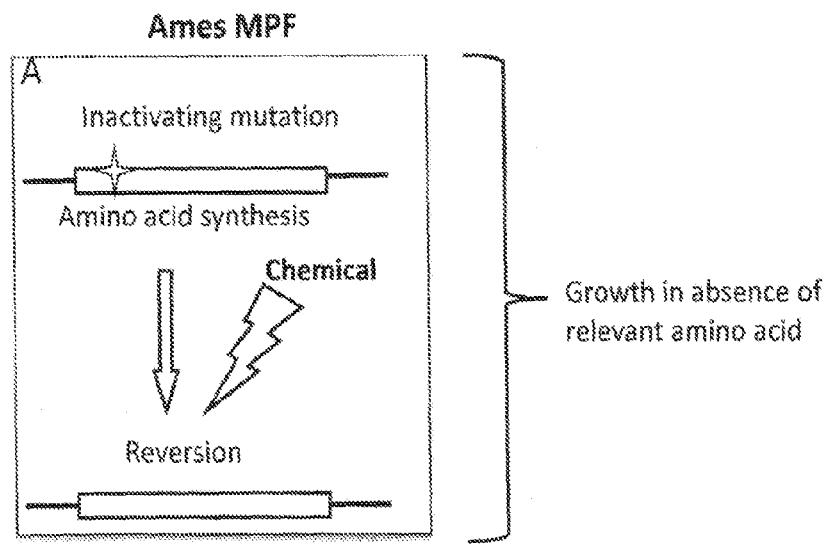
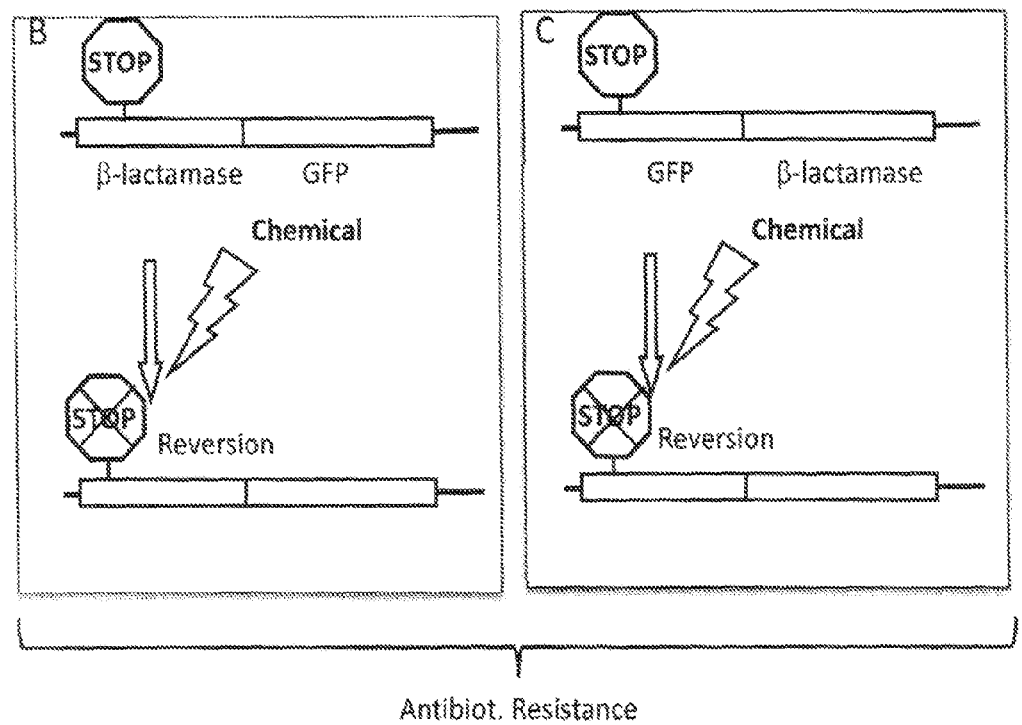

Fig. 1b Comparison between binary and quantitative readout
Binary readout: growth vs. no growth
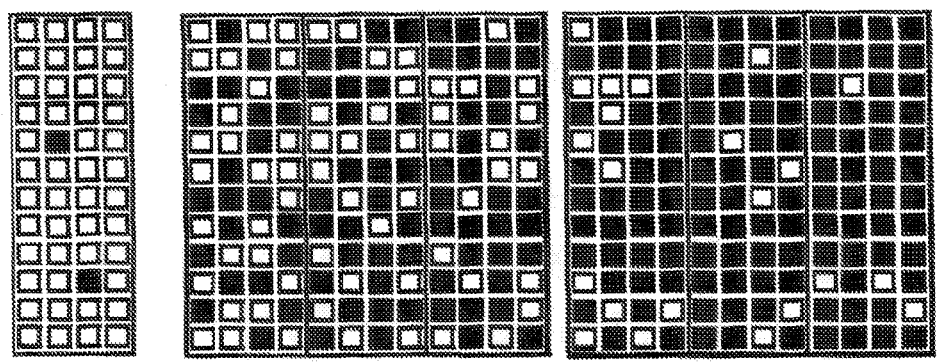
Control　　　　Mutagen
Quantitative readout: fluorescence
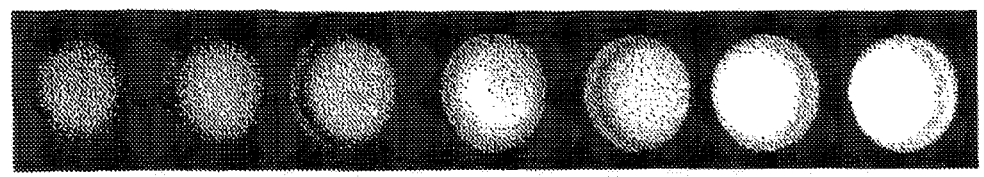
Control　　　　Mutagen

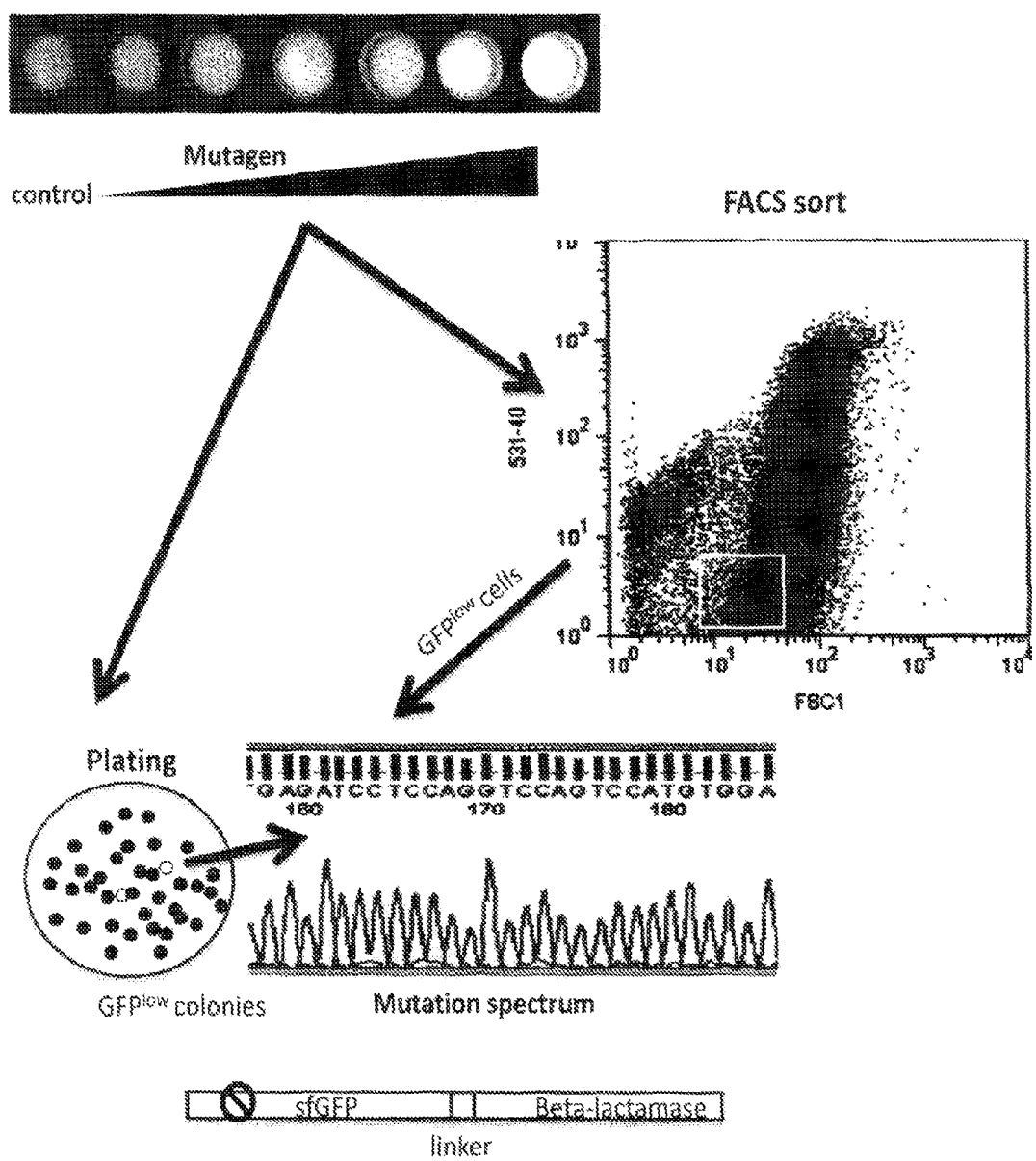

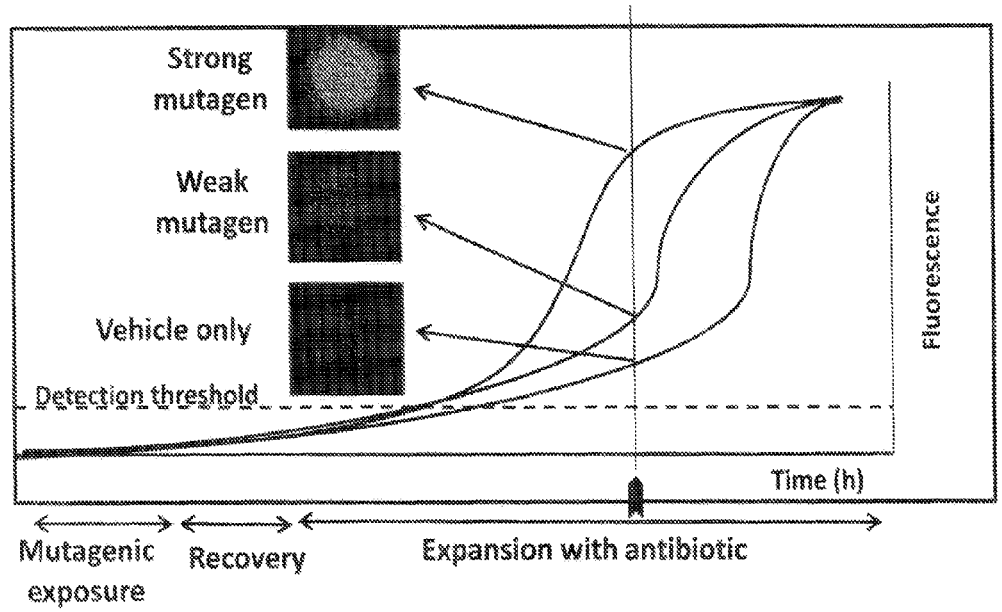
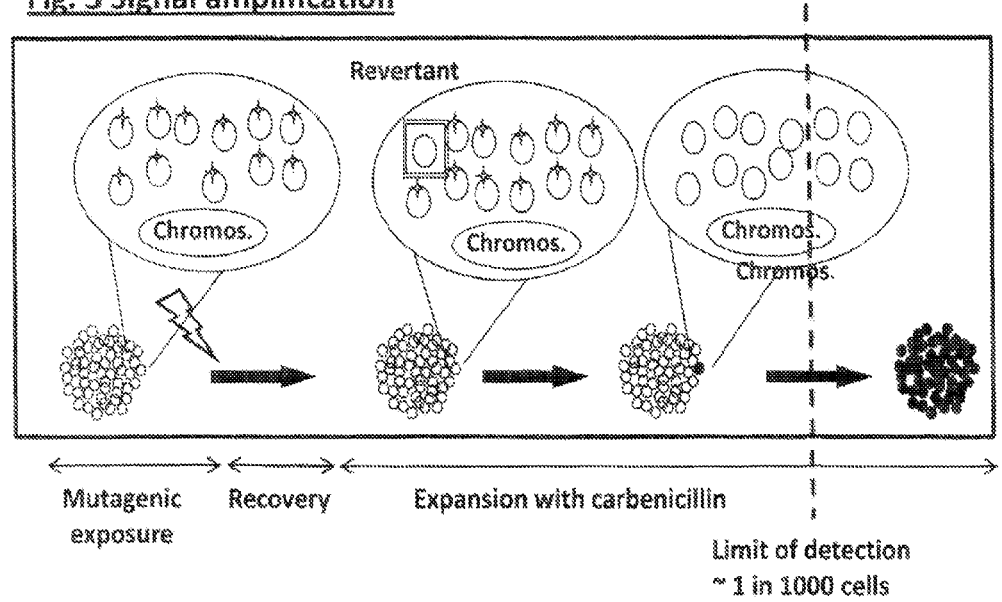

Fig. 4 Generation of dual-function fusion protein
a
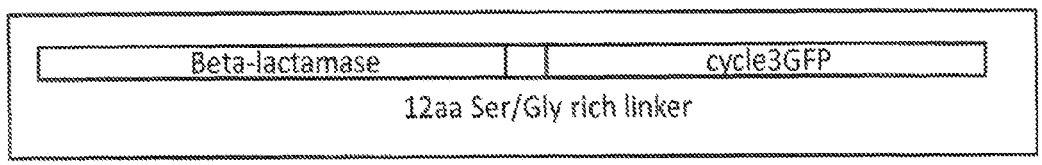
b
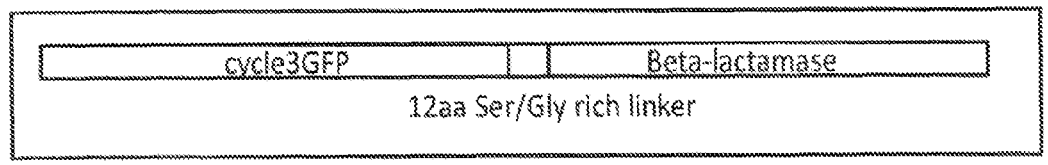
c
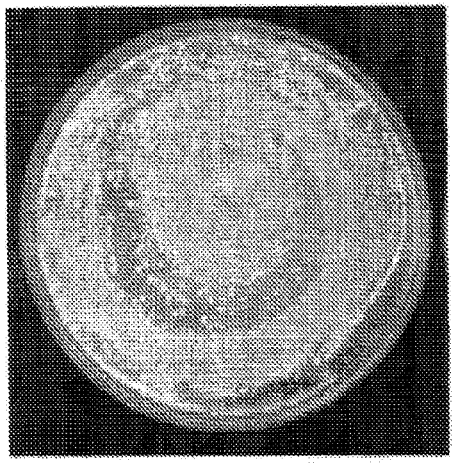

Fig. 5 Effect of replacing cycle 3 GFP by sfGFP
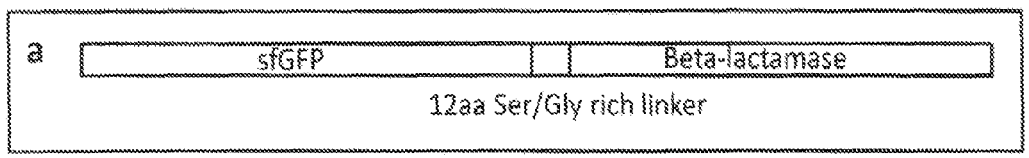
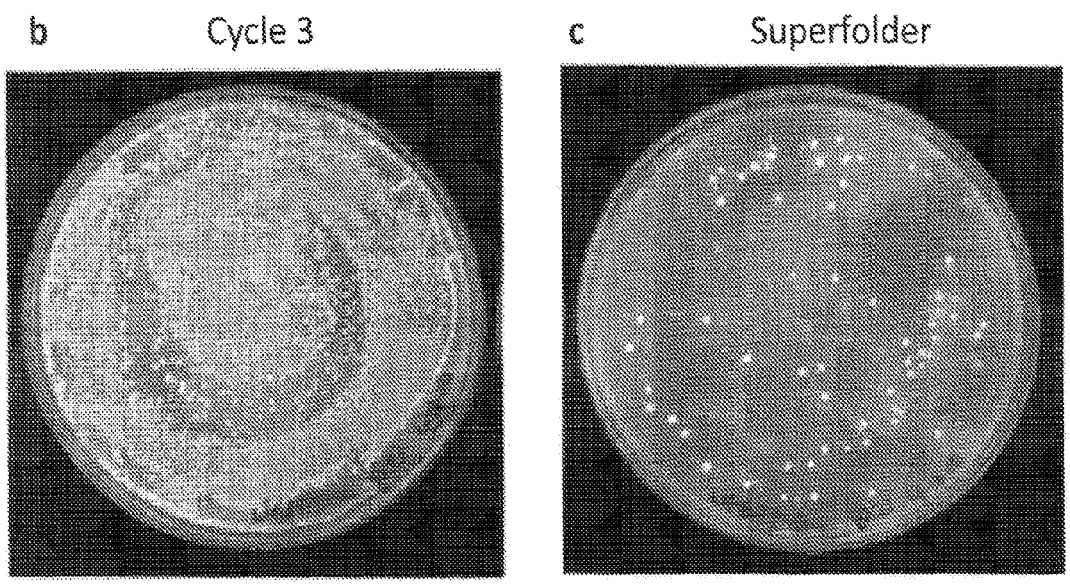
b  Cycle 3          c  Superfolder

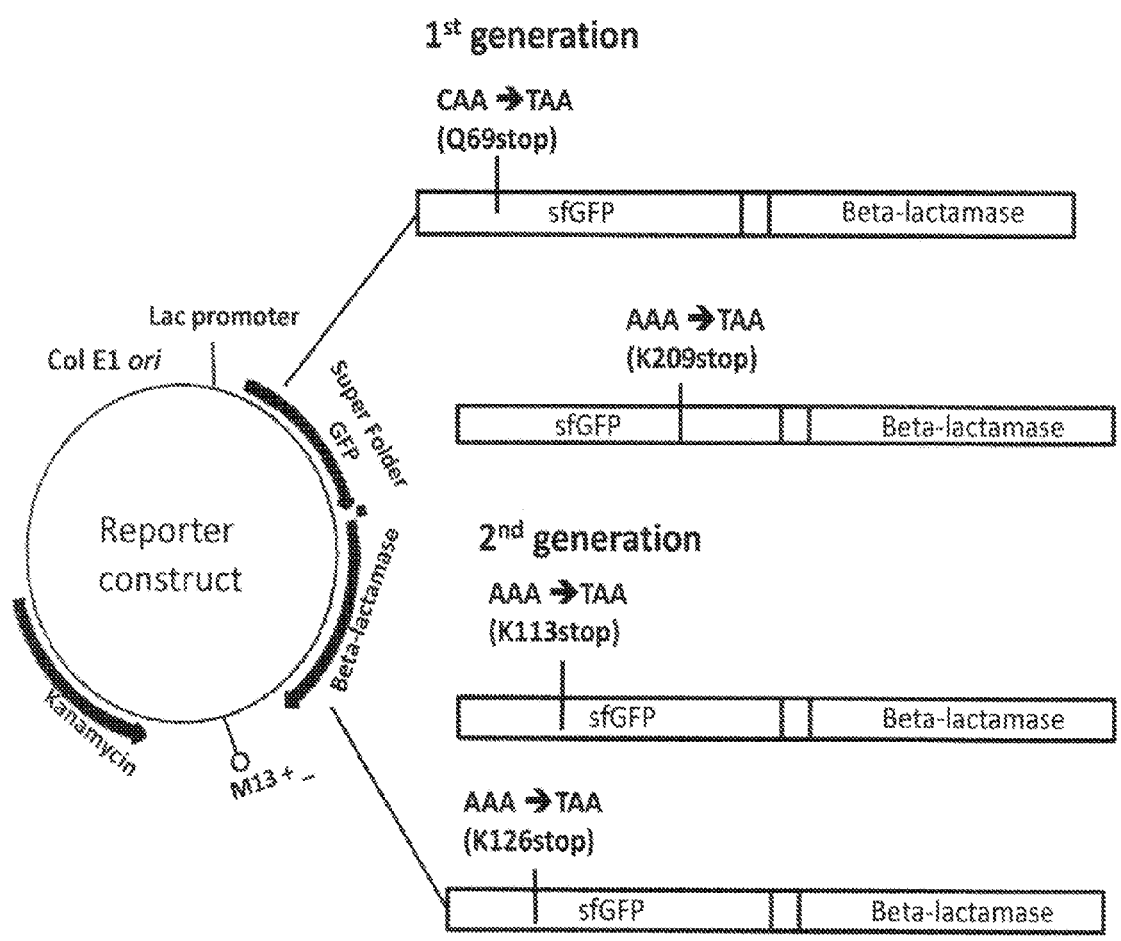
Fig. 6 Generation of reversion mutagenesis reporter

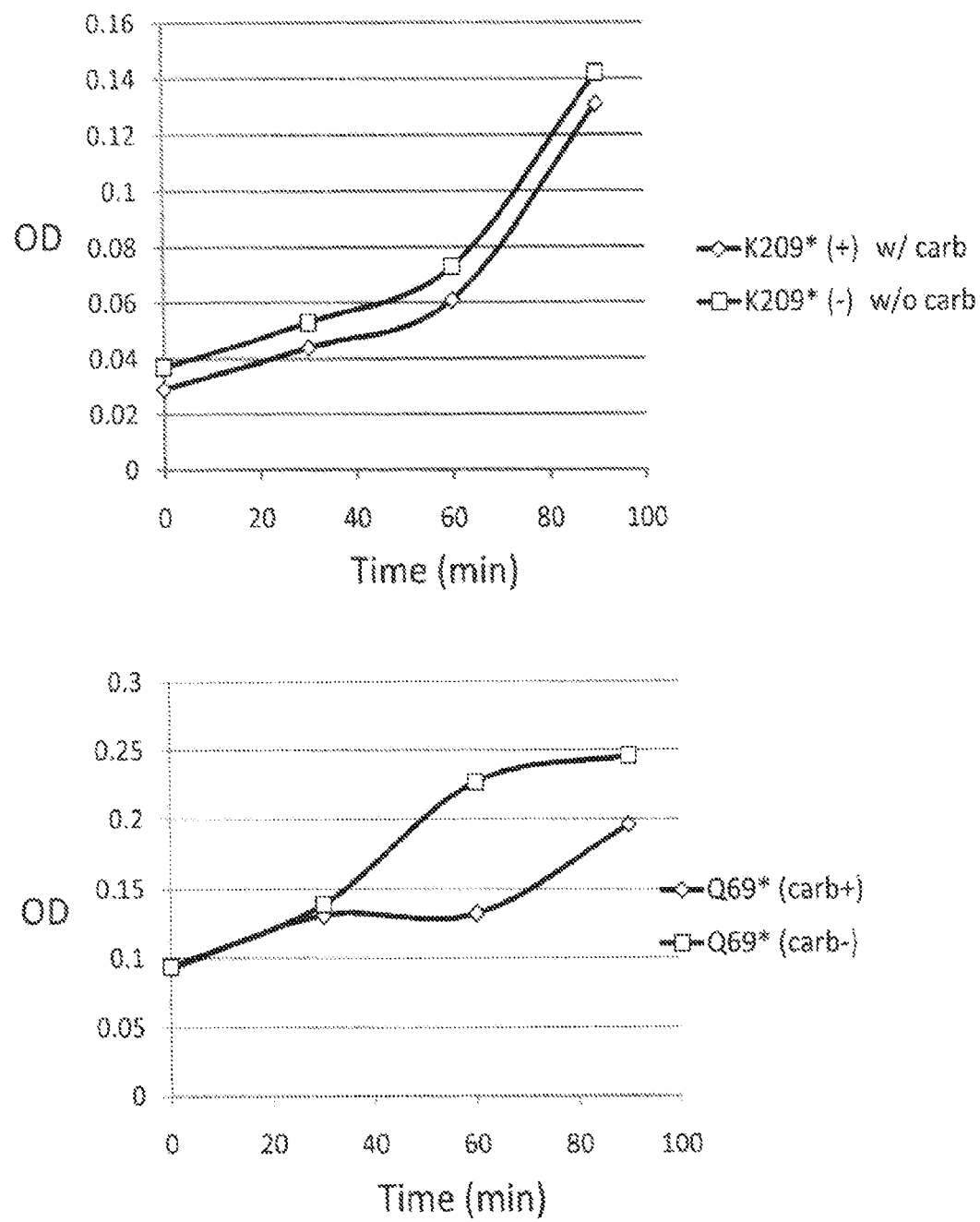

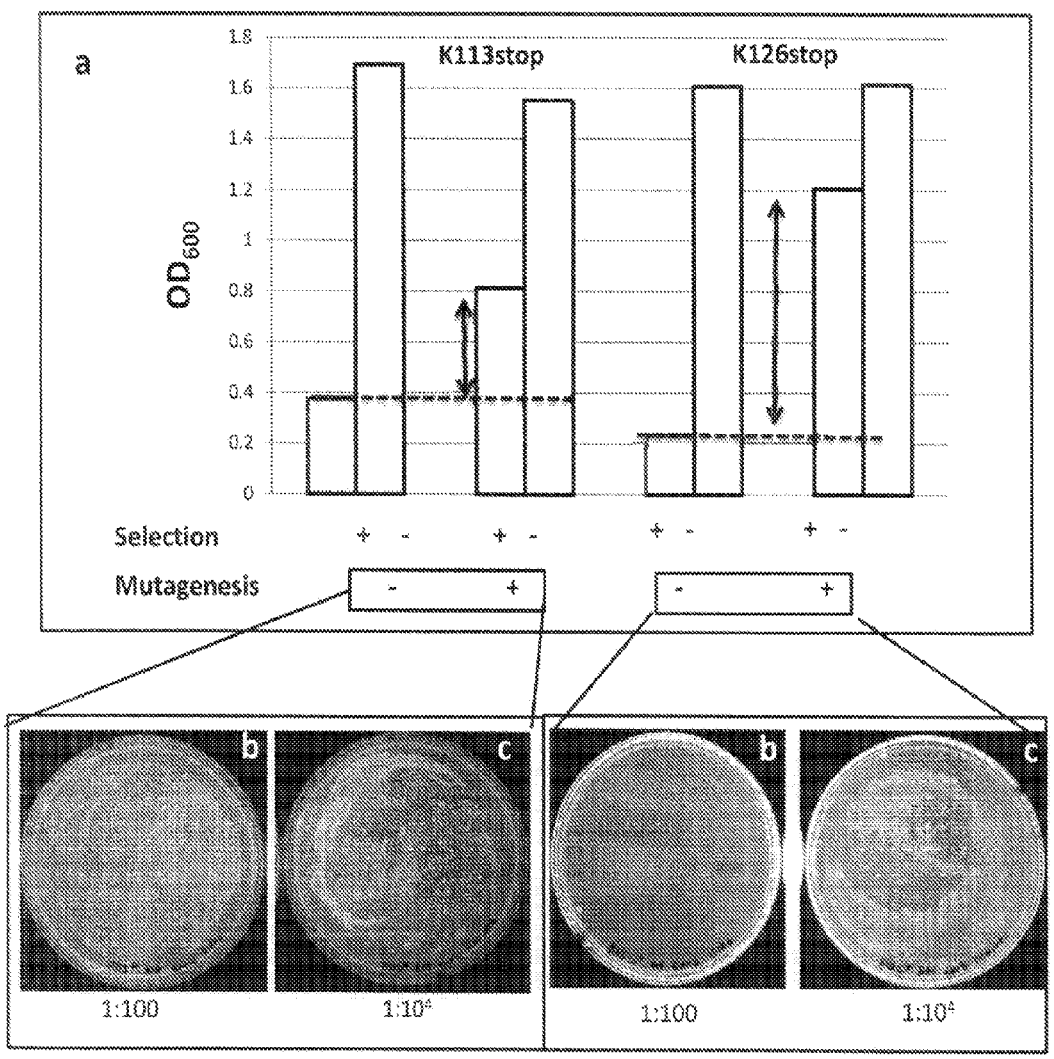

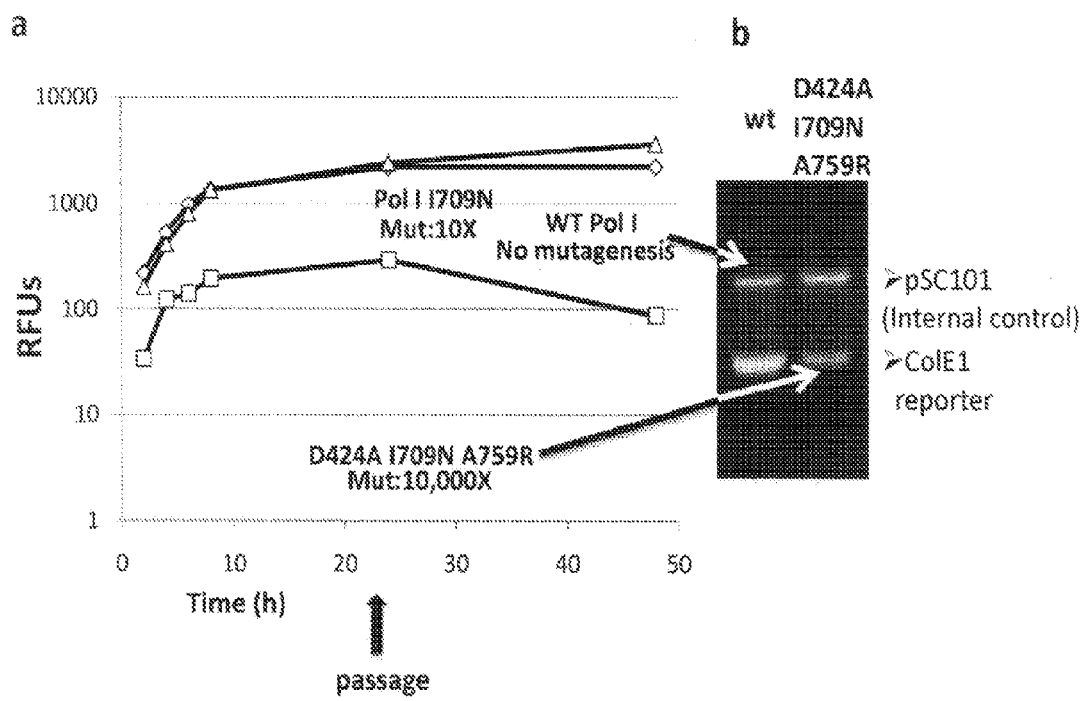

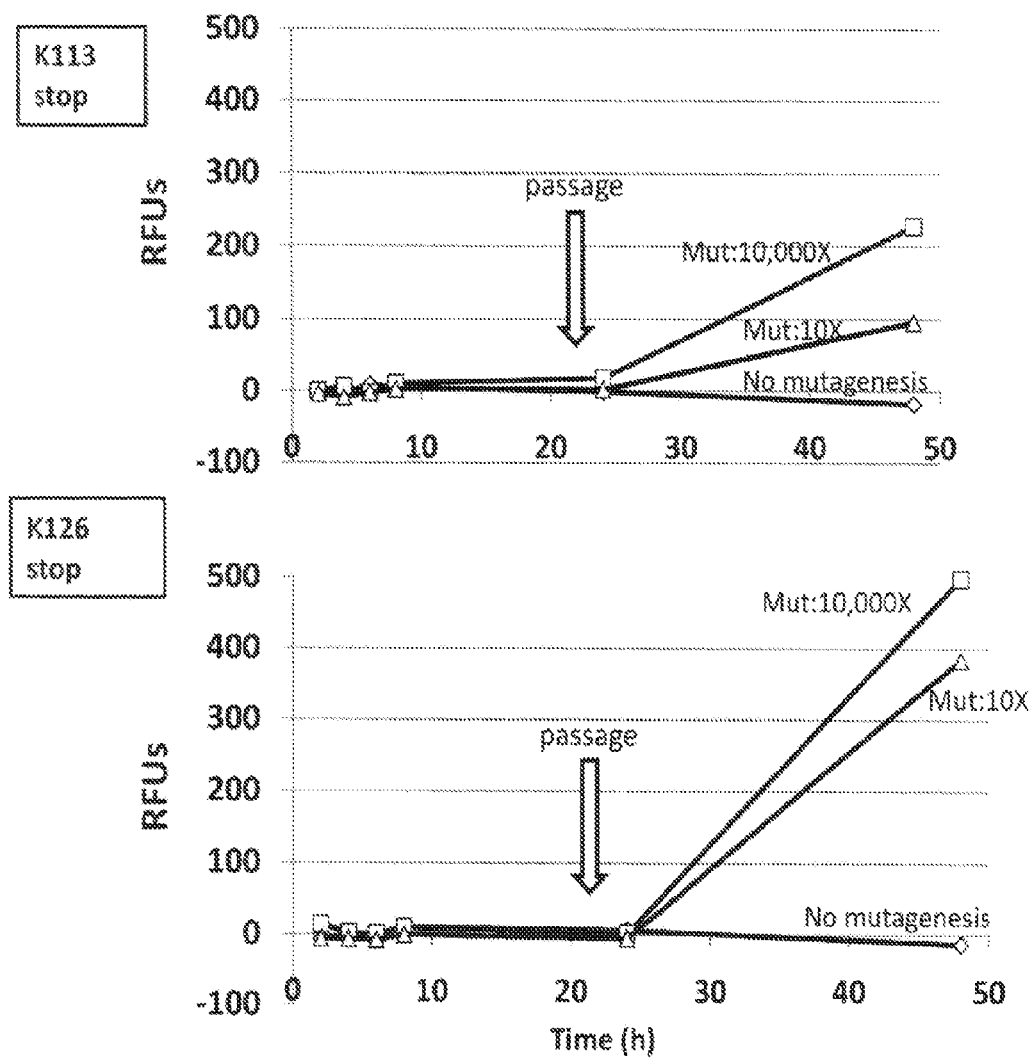
Fig. 10 Mutagenesis detection

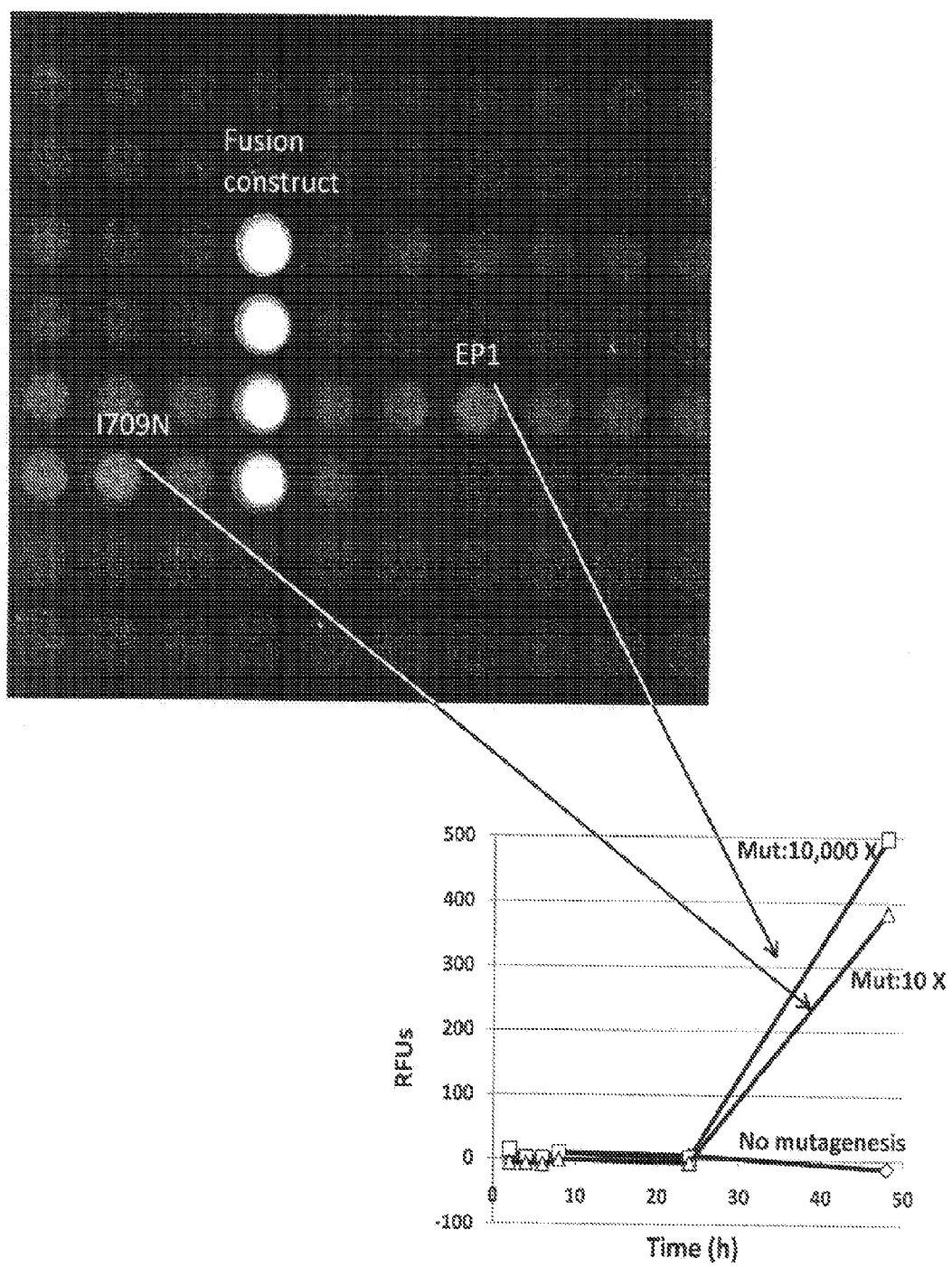
Fig. 11 Mutagenesis detection through a gel imaging system

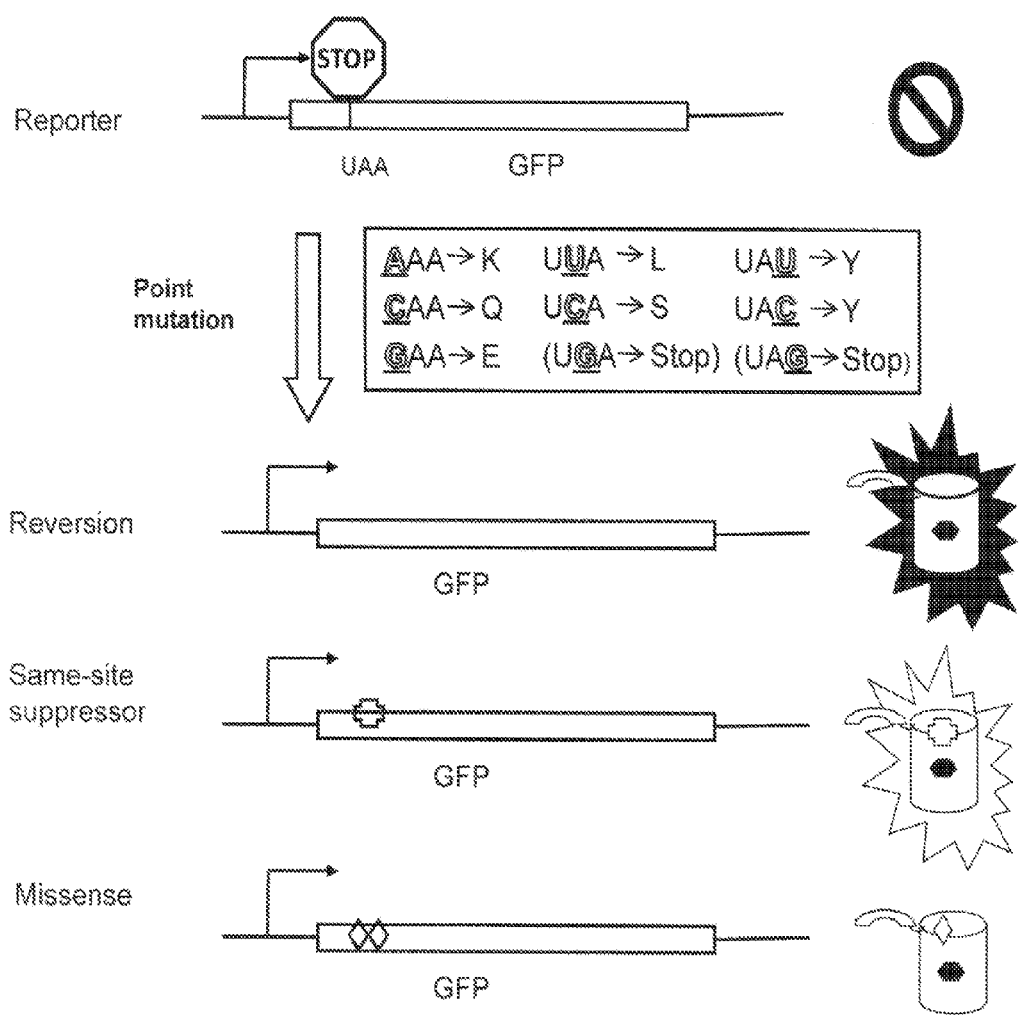

Fig. 13: Sequence ID No. 1 as shown in Fig. 1c.

<110> The Regents of The University of California
    CAMPS, Manel

<120> Sensitive Detection of Mutations for Drug and Environmental Screening

<130> UCSC2010-252 WO

<140> US61/257,080
<141> 2009-11-02

<140> US61/363,296
<141> 2010-07-12

<160> 1

<210> 1
<211> 28
<212> DNA
<213> Artificial Sequence

<220>
<223> Aequorea victoria

<400> 1
gagatcctcc aggtccagtc catgtgga

GFP MUTAGENESIS AMPLIFICATION: USE OF A FLUORESCENCE-ANTIBIOTIC RESISTANCE FUSION DUAL REPORTER CONSTRUCT TO PROVIDE QUANTITATIVE AND HIGHLY SENSITIVE DETECTION OF MUTATIONS

RELATIONSHIP TO OTHER APPLICATIONS

The present application claims the benefit of and priority to U.S. provisional application No. 61/257,080, filed 2 Nov. 2009 and to U.S. provisional application No. 61/363,296, filed 12 Jul. 2010, both of which are incorporated by reference in its entirety for all purposes.

STATEMENT OF SUPPORT

This invention was made with government support under the following grants: NIH 7K08CA116429-01A1 and UCSC Start-up 20095 Educational Fee Outlay, 19900 General State Appropriations. The government has certain rights in the invention.

SEQUENCE LISTING

The information recorded in electronic form (if any) submitted with this application (under Rule 13ter if appropriate) is identical to the sequence listing as contained in the application as filed.

FIELD OF THE INVENTION

Detection of very rare mutations in polynucleotides using a reversion mutation assay based on the creation of a functional GFP-β-lactamase fusion protein as a reporter providing both antibiotic resistance and fluorescence.

BACKGROUND

The Ames' test is the most widely-used genotoxicity assay and is required by regulatory agencies for the registration and approval of new chemicals. This assay is performed in *Salmonella*, but is considered a good indicator of genotoxicity for mammalian systems, because DNA damage and repair mechanisms are conserved between bacteria en humans. Indeed, the Ames' test exhibits the highest sensitivity for detection of carcinogenesis in rodents of all standard genotoxicity tests.

The Ames' Test is a mutation reversion test. The specific reversion site is an inactivating mutation in an amino acid biosynthesis operon. Mutagenesis is detected as growth in the presence of limiting amounts of the relevant amino acid. The assay can be performed on solid plates (Ames' plate incorporation test) or in liquid version (Ames' fluctuation assay). The main problem is the large amount of compound required. Even the miniaturized versions of Ames: mini-Ames (solid), and Ames II and MPF (liquid), require >10 mg amounts of test compound, which limits the use of this assay to detect mutagenic activity during early stages of drug discovery (when typically little amount of compound is available) or in complex mixtures of compounds, (where the active compound may be a small fraction of the total). The required sample amount also limits the ability for biomonitoring environmental mutagens in typical environmental mixtures The present invention is based on the same principles as Ames test but is far more sensitive and provides quantitative information. The inventors have developed a novel method for detection of chemical mutagenesis that requires only a fraction of the sample used in Ames (at least 100-fold less). The present method can be used for drug discovery and for environmental biomonitoring. Also it may be used to screen high-yield natural products libraries for compounds targeting DNA as potential antimicrobial, anti-inflammatory or antitumor agents.

BRIEF DESCRIPTION OF THE INVENTION

Specifically, the invention encompasses a method for detecting and quantitavely measuring the mutagenic potency of a test substance. The method specifically includes the following:

A method for detecting and quantitavely measuring the mutagenic potency of a test substance, the method comprising:

1) providing a test substance,
2) providing a functional fluorescence-antibiotic resistance fusion construct to act as a dual reporter, wherein the dual reporter possesses a reversion site upstream of (at the N-terminus of) the fluorescence-antibiotic resistance fusion operons, wherein the dual reporter is cloned into a multicopy plasmid, and wherein mutations at the reversion site allow read-through of the fusion protein producing both an antibiotic resistance protein and a fluorescent protein, and further wherein, in the presence of an antibiotic, the production of the antibiotic resistance protein confers a selective advantage that causes amplification of mutant plasmids, thereby raising the level of fluorescence emitted by the fluorescence protein to levels that are detectable by fluorimetry, wherein fluorescence is proportional to the number of mutation events at the reversion site,
3) transforming a host cell with the multicopy plasmid,
4) contracting the host cell to the test substance to induce mutations at the reversion site,
5) amplifying the plasmids that have mutations at the reversion site,
6) measuring the fluorescent signal, wherein the amplitude of the fluorescent signal is quantitavely proportional to the number of mutation events at the reversion site and therefore to the mutagenic potency of the test substance.

Defining the fluorescence-antibiotic resistance fusion construct more specifically, the invention includes:

A method for detecting and quantitavely measuring the mutagenic potency of a test substance, the method comprising:

1) providing a test substance,
2) providing a functional GFP-beta-lactamase fusion construct to act as a dual reporter, wherein the dual reporter possesses a reversion site at the N-terminus, wherein the dual reporter is cloned into a multicopy plasmid, and wherein mutations at the reversion site allow read-through of the fusion protein producing both beta-lactamase and GFP, and further wherein, in the presence of an antibiotic, beta-lactamase production confers a selective advantage that causes amplification of mutant plasmids, thereby raising the level of fluorescence emitted by GFP to levels that are detectable by fluorimetry, wherein fluorescence is proportional to the number of mutation events at the reversion site,
3) transforming a host cell with the multicopy plasmid,
4) contracting the host cell to the test substance to induce mutations at the reversion site,
5) amplifying the plasmids that have mutations at the reversion site,
6) measuring the fluorescent signal, wherein the amplitude of the fluorescent signal is quantitavely proportional to the number of mutation events at the reversion site and therefore to the mutagenic potency of the test substance.

In either method, the assay is sufficiently sensitive to detect mutation frequencies as low as 1 in $10^8$ nucleotides.

In various preferred embodiments the method specifically does not use GFP as a transcriptional reporter, unlike the presently known GFP-based genotoxic tests.

In another embodiment the amplitude of the fluorescent signal of the assay is proportional to mutation frequency after normalization for differences in copy number.

In another embodiment the reversion mutants are amplified in two steps: (i) the mutant plasmid becomes homoplasmic, and (ii) the reversion mutant cells grow preferentially in culture under antibiotic selection.

In another embodiment the selection antibiotic is bacteriostatic but not bacteriocidal.

In another embodiment the GFP is superfolder green fluorescent protein.

In another embodiment the functional expression of beta-lactamase gene is suppressed.

In another embodiment the mutagenic effect can be determined as the area under the curve of fluorescence relative to that of an untreated control representing spontaneous mutations.

In another embodiment the method is performed as part of high-throughput screening for DNA-targeting compounds.

In another embodiment the method is performed using 96-well-format.

Another composition embodiment is a fluorescence-antibiotic resistance fusion dual reporter construct, wherein the dual reporter possesses a reversion site at the N-terminus, wherein the dual reporter is adapted to be cloned into a multicopy plasmid, and wherein mutations at the reversion site allow read-through of the fusion protein producing both and antibiotic resistance protein and a fluorescent protein. The antibiotic resistance gene may confer resistance against beta lactam antibiotics and the fluorescence protein may be GFP. In another embodiment the fluorescence-antibiotic resistance fusion dual reporter construct may be cloned into a multicopy plasmid.

In some embodiments the reporter construct may be integrated into an extra-chromosomal expression vector such as a self replicating plasmid, while in other embodiments the expression construct may be integrated into another type of polynucleotide such as a chromosome of the host cell. If practicing the mutagenesis assay in such a way that the expression construct is integrated into a chromosome rather than into a plasmid, a larger number of transformed cells will be required in the assay to make up for the decreased number of targets and still allow detection of the fluorescent signal.

More generally, the invention encompasses a novel reversion mutation assay that is unique in providing a quantitative readout for mutagenesis. This assay, which we named 'GFP fluorescence Amplification Mutation (GAM) assay' is based on the creation of a functional GFP-β-lactamase fusion protein as a reporter providing both antibiotic resistance and fluorescence. This dual reporter is placed in a multicopy plasmid to increase the number of targets, with a reversion site at the N-terminus. Rare mutations at the reversion site allow read-through of the fusion protein, producing both beta-lactamase (providing antibiotic resistance) and GFP (emitting fluorescence). In the presence of carbenicillin, beta-lactamase production confers a selective advantage that allows amplification of mutant plasmids, raising the level of fluorescence emitted by GFP to levels that are detectable by fluorimetry. A window of time can be found where fluorescence is proportional to the number of mutation events at the reversion site, making fluorescence a quantitative measure of mutagenesis. Quantitative (as opposed to binary) detection of mutations allows substantial savings in test sample. This has applications in drug discovery, allowing high-throughput screening for DNA-targeting compounds (with potential anti-tumor and antimicrobial properties) and early pre-screening of leads for potential carcinogenic activity. The increased sensitivity of this assay also facilitates monitoring complex environmental samples. This assay is adaptable to 96-well-format, to detection of frameshift mutations, and to detection of pro-carcinogens through addition of S9 fraction.

The invention encompasses a system that detects the appearance of rare mutations (in the order of 1 in $10^8$ nucleotides) by reversion of a drug-selectable marker coupled to a fluorescent, luminescent or colorimetric marker in live cells. The mutations can be induced by chemicals, by error-prone polymerases or be spontaneous.

The system detects new mutations, not the presence of mutations relative to a reference sequence. In the present disclosure, we use, as an example, detection of mutations introduced by an error-prone polymerase in *E. coli* cells, as an antibiotic marker we use the bla gene, encoding beta-lactamase, and as reporter green fluorescent protein. The dual reporter is encoded in a high-copy plasmid. Reversion to antibiotic resistance allows amplification of the signal (first inside the cell, and then within the population), and the coupled reporter allows detection by fluorometry or spectrophotometry or colorimetry (FIG. 3 of update).

The principle of the assay is the same as that of the Ames' test. Both assays are based on genetic reversion. The difference is the number of targets ($10^9$ compared to $10^7$ for Ames) and the readout, which for Ames in liquid culture is based on fluctuation analysis whereas my readout is directly quantitative. This dramatically decreases the sample size and allows new applications of genetic reversion assays including, for example, 1. Drug pre-screening for potential carcinogenesis in early stages of development, when typically only a small number of compound is available. This allows eliminating compounds from the development pipeline early on, when they still don't carry a heavy investment.

2. Enriching chemical libraries for biological activity. The main problem of chemical libraries is that the fraction of active compounds is exceedingly small (less than 1 in $10^8$). This assay provides a way to enrich these libraries for compounds with biological activity that can be used for the biological screens of interest. Mutagenesis in this case would be a side-effect, it could be solved by derivatization in later stages of development.

3. Screening chemical or natural products libraries for compounds that target DNA, as potential anti-inflammatory, antimicrobial and antitumor agents.

In addition the assay improves ability to biomonitor environmental samples, i.e. to detect mutagens in complex environmental samples (as the relevant compound may be only a small fraction of the total).

An important novel aspect of the invention is the use of the double amplification process that allows detection of a single, very rare mutations (1 in $10^8$ at most) by fluorimetric means. The detection data produced are quantitative and integrates a significant number of independent events into a single experiment. Thus the readout is proportional to the mutagenic effect and uses only a fraction of the sample, so is much more sensitive and accurate than the standard Ames test.

A preferred embodiment of the invention employs a Green fluorescence Amplification Mutation (GAM) assay, which is unique in providing a quantitative readout for mutagenesis.

This GAM method is based on a reporter plasmid bearing beta-lactamase fused to green fluorescent protein. Reversion of an inactivating mutation at the N-terminus of the fusion construct leads to both antibiotic resistance and fluorescence that can be detected by fluorimetry or by standard gel imaging systems. However, both the creation of the dual function reporter and the position of the stop codons to create reversion sites for mutagenesis required a significant amount of optimization: (1) GFP folding had to be stabilized (through the use of superfolder GFP). (2) Functional expression of beta-lactamase in our reversion mutagenesis reporter had to be suppressed. We achieved this partially by rational design (looking for an area of the protein which was poor in methionine residues, as potential alternative start codons) and partially by trial and error.

The GMA assay was validated through expression of a panel of low-fidelity DNA polymerase I mutants. DNA polymerase I initiates leader strand synthesis in our reporter plasmid, introducing mutations at a known frequency. This avoids problems of toxicity associated with the use of chemical mutagens while facilitating control of the mutation load. We established that the fluorescent signal of the assay correlates with mutation frequency (after normalization for differences in copy number) and that GMA exhibits exquisite sensitivity, detecting mutation frequencies as low as 1 in $10^8$. This frequency is only 10 times higher than the spontaneous mutation rate in E. coli.

In summary, the mutagenesis assay is conceptually similar to the Ames' test but produces a quantitative rather than a binary signal. Therefore this assay allows large savings in reagents and, more important, test sample. GMA is therefore ideally suited for situations in which sample is limiting, such as early stages of drug development or for biomonitoring of complex environmental samples.

BRIEF DESCRIPTION OF THE FIGURES

FIG. 1a Comparison between Ames MPF and GAM
FIG. 1b Comparison between binary and quantitative readout
FIG. 1c Use of GAM as a forward mutation assay
FIG. 2 Signal detection
FIG. 3 Signal amplification
FIG. 4 Generation of dual-function fusion protein
FIG. 5 Effect of replacing cycle 3 GFP by sfGFP
FIG. 6 Generation of reversion mutagenesis reporter
FIG. 7 First-generation reversion mutagenesis reporters
FIG. 8 Second-generation reversion mutagenesis reporters
FIG. 9 Fluorescence detection: positive control
FIG. 10 Mutagenesis detection
FIG. 11 Mutagenesis detection through a gel imaging system
FIG. 12 Stop mutations
FIG. 13 Sequence ID No. 1 as shown in FIG. 1c.

The sequence listing for SEQ ID No. 1 as shown in FIG. 1c is as follows:
<110> The Regents of The University of California CAMPS, Manel
<120> Sensitive Detection of Mutations for Drug and Environmental Screening
<130> UCSC2010-252 WO
<140> U.S. 61/257,080
<141> 2009 Nov. 2
<140> U.S. 61/363,296
<141> 2010 Jul. 12
<160> 1
<210> 1
<211> 28
<212> DNA
<213> Artificial Sequence
<220>
<223> Aequorea victoria
<400> 1
gagatcctcc aggtccagtc catgtgga

GENERAL REPRESENTATIONS CONCERNING THE DISCLOSURE

The embodiments disclosed in this specification are exemplary and do not limit the invention. Other embodiments can be utilized and changes can be made. As used in this specification, the singular forms "a", "an", and "the" include plural reference unless the context clearly dictates otherwise. Thus, for example, a reference to "a part" includes a plurality of such parts, and so forth. The term "comprises" and grammatical equivalents thereof are used in this specification to mean that, in addition to the features specifically identified, other features are optionally present. Where reference is made in this specification to a method comprising two or more defined steps, the defined steps can be carried out in any order or simultaneously (except where the context excludes that possibility), and the method can optionally include one or more other steps which are carried out before any of the defined steps, between two of the defined steps, or after all the defined steps (except where the context excludes that possibility). Where reference is made herein to "first" and "second" features, this is generally done for identification purposes; unless the context requires otherwise, the first and second features can be the same or different, and reference to a first feature does not mean that a second feature is necessarily present. Where reference is made herein to "a" or "an" feature, this includes the possibility that there are two or more such features. This specification incorporates by reference all documents referred to herein and all documents filed concurrently with this specification or filed previously in connection with this application, including but not limited to such documents which are open to public inspection with this specification.

DEFINITIONS

A "Test compound" can be a single compound, a mixture of compounds or a (synthetic or natural products) library of compounds. A test compound can contact the tester strain in a variety of physical states: in solution, insoluble or even gas. A mutagen includes any physical or chemical agent capable of increasing frequency of mutation above the spontaneous, background level.

DETAILED DESCRIPTION OF THE INVENTION

The present invention is based on the same principles as Ames (genetic reversion) but uses only micromolar amounts of test compound because of a quantitative readout and two amplification steps (see Table 1). Use of the invention allows higher sensitivity detection and quantitative detection of mutagens, and provide significant cost-saving. The invention provides a mutagenesis assay that uses only a fraction of the sample required for the traditional Ames' test. It is well suited for drug discovery and environmental biomonitoring. Proof of concept is disclosed showing detection of mutations introduced by an error-prone polymerase.

A preferred embodiment encompasses a method employing a GFP Mutagenesis Amplification (GMA) assay, which provides a quantitative readout for mutagenesis, minimizing the amount of sample required and facilitating high-throughput formats.

We have established that the limit of detection is between 1 in 1,000 and 1 in 10,000 fluorescent cells in culture using a standard fluorometer.

readout that should require only a fraction of the test sample necessary for Ames'-based tests.

Our assay makes mutagenesis testing practicable in situations in which the amount of sample may be limiting such as testing lead compounds in early stages of development or biomonitoring the presence of mutagens in the environment. Additionally the assay is accurate, sensitive, reliable, simple to perform and inexpensive.

TABLE 1

Advantages of the GAM assay over Ames' Test

| Categories | Ames | Ames liquid | GAM | Advantage |
|---|---|---|---|---|
| Reversion | Auxotrophic marker | Auxotrophic marker | Antibiotic resistance | |
| Location | Chromos. | Chromos. | Plasmid | 100-fold increase in target size. Amplified by selection. |
| Selection | Growth on agar lacking relevant amino acid (colonies) | Growth in liquid media lacking relevant amino acid. | Growth in carbenicillin | Allows growth in rich media, producing results in 24 h as opposed to 48 h |
| Readout | | Colorimetric (fluctuation analysis) | Fluorescence (quantitative) | Integrative (sum of multiple events). Wider dynamic range (detection of at least 1 cell in $10^3$ cells). |
| Spectrum | Specific target for reversion | Specific target for reversion | Can be used as forward mutation assay | Spectrum not limited by reporter target; can detect hotspots |
| Scalable | No | Yes | Yes (except forward mutation) | Cost-saving opportunity |

Novel aspects of the invention include the double amplification process that produces a quantified fluorimetric signal from a single, very rare event (1 in $10^8$ or less). We know of no other instance of measurement of a rare mutational reversion event by fluorimetry in liquid culture. Indeed, precisely because this level of detection is so technically challenging, other recent GFP-based genotoxic tests used GFP as a transcriptional reporter instead, even though this is less specific than detecting mutations by fluorimetry (see U.S. Pat. No. 6,667,153 and 20070224609). Coupling a reversion to a forward mutation assay and separating the target from the reversion assay (in this case, beta-lactamase) from that of the forward mutation assay is, we believe, entirely novel.

In one embodiment we present a 'Green fluorescence Amplification Mutation assay' (GAM assay), which provides a quantitative readout for mutagenesis using fluorimetry. Our GAM assay is based on a reporter plasmid bearing beta-lactamase fused to green fluorescent protein. Beta-lactamase carries a stop codon. Rare mutations targeting the stop codon allow read-through of the fusion protein, producing both beta-lactamase (providing antibiotic resistance) and GFP (emitting fluorescence). This provides a selective advantage in the presence of carbenicillin that allows amplification of plasmids carrying the relevant mutation, which in turn is detected through the fluorescence emitted by GFP. Thus, fluorescence is quantitavely proportional to the number of stop codon mutation events in the culture, and therefore represents a quantitative measure of mutagenesis.

Using a panel of error-prone DNA polymerase I mutants with known mutation rates, we have confirmed a correlation between fluorescence emission and mutation rates and established detection of as little 1 mutation in $10^8$ plasmids.

The GAM assay disclosed, therefore, provides a simple yet highly sensitive assay for mutagenesis with a quantitative Methods The foundational method of the invention is an assay that provides detection of very rare mutation events. The assay (named GAM for GFP-Amplification Mutagenesis detection assay) is based on a dual reporter bearing beta-lactamase linked to a fluorescent reporter (GFP) and a specific reversion site. Reversion produces both carbenicillin resistance and fluorescence (FIG. 1a and FIG. 2).

Unlike the liquid Ames test, which is based on fluctuation analysis, the present invention uses a reporter that produces an accurate quantitative readout. This concept is illustrated in FIG. 1b. Fluctuation assays detect rare random events, and therefore require a multiplicity of independent experiments. This quantitative readout integrates a significant number of independent events in a single experiment. This makes the readout proportional to the mutagenic effect and uses only a fraction of the sample.

A quantitative readout is only possible because the invention increases the target population 1,000-fold by placing the reporter in a multicopy plasmid (about 100 copies/cell) and also starts with a larger number of cells than liquid Ames ($10^8$ compared to $10^7$). Reversion mutants are amplified in two steps: in the first step, the mutant plasmid becomes homoplasmic, i.e. becomes the sole species in the cell, and in the second step, reversion mutant cells grow preferentially in culture under antibiotic selection (FIGS. 2 and 3). Thus, in each test sample we are looking at a much larger number of events than we would in a liquid Ames. Note that we use as a selectable marker carbenicillin, which is an antibiotic with static rather than cidal activity to extend the window of time during which cells can mutate. Note also that with a larger number of targets $>10^7$, we expect detection of spontaneous mutations. This will provide a baseline for the assay to quantify the overall mutagenic effect (FIG. 2).

In the current invention, a Reversion mutation produces both antibiotic resistance and fluorescence (FIG. 1a and FIG. 2). When mutant cells reach a threshold in the population (~1 in 1000), they can be detected by fluorescence. Fluorescence is monitored over a period of time. The mutagenic effect can be determined as the area under the curve of fluorescence relative to that of an untreated control representing spontaneous mutations. Further, GFP$^{low}$ mutants can be isolated and sequenced for an accurate determination of mutation spectrum (FIG. 1b).

EXAMPLES AND FURTHER EXPERIMENTAL WORK

Determining Assay Sensitivity to Chemical Mutagens. $10^8$ cells were tested with three potent inducers of base-pair substitutions. The cells were exposed to each of 4-nitroquinoline N-oxide (4-NQO), propiolactone, and N-Nitroso n-methylurea (NMU) for 90 minutes (exposure phase), diluted out 100-fold in rich media with carbenicillin, allowed to grow for 4 h (amplification phase) and then aliquots taken at 15-minute intervals until the control reaches saturation (readout phase). Aliquots are be washed and resuspended in PBS prior to fluorometry reading to eliminate the autofluorescence generated by amino acids present in media. Differences in the "area under the curve" are then determined in the treated cultures relative to untreated controls and establish dose-dependence (FIG. 4).

Demonstrating Detection of Metabolic Activation.

During the exposure phase, cells may be incubated with a reference chemical requiring metabolic activation (benzopyrene or nitrosamine) for 90 minutes in the presence of S9 fraction. The rest of the assay may be performed as described for Specific aim 1.

Demonstrating Detection of Frameshifts.

90% of all mutagens can be detected by a combination of a base-pair substitution and a −1 frameshift reporters. We may introduce a −1 frameshift nearby a CG-rich stretch in the beta lactamase sequence. The new reporter may be tested using a strong frameshift mutagen (2-nitrofluorene) using the procedures described above.

Determining Range of Chemical Detection.

We may use a set of reference chemicals previously used to validate the Ames II Assay (M. Kamber, Mutagenesis 24 (2009) 359-366), which include weak mutagens and mutagens requiring metabolic activation.

Adapting the Assay to 96-Well Format.

The assay may be adapted to a microplate format, which is the format routinely used for high throughput screening by pharmaceutical companies. Each plate may include the two reporter strains exposed to six different doses of test compound (including one mock-treated control) with and without S9 fractions (2×6×2=24 wells) in triplicate (24×3=72) wells.

As hosts we may use DJ701 cells, which are a E. coli cell host comparable to Salmonella strains used for the Ames' test, as they have an inactive uvr operon (and are therefore deficient in nucleotide excision repair), lack a lipopolysaccharide (LPS) coat and have strong umu operon expression (P. D. Josephy The Escherichia coli lacZ reversion mutagenicity assay, Mutat Res 455 (2000) 71-80).

Alternative Embodiments and Methodological Variations

The frameshift reporter works because detection is based on reversion. However, the frameshift frequency at the reporter site may be low because frameshifts are notoriously sensitive to sequence context. In an alternative embodiment, if the engineered reporter performs poorly one may identify sites that mutate in response to frameshift-inducing agents and screen for loss of carbenicillin resistance by exposing a plasmid carrying kanatmycin and carbenicillin resistance markers to the frameshift-inducing mutagen and looking for kanamycin-resistant colonies that are sensitive to carbenicillin. To create the frameshift-sensitized reporter, the most frequently mutated site may be introduced as a reversion site into the beta-lactamase portion of the dual reporter.

Even though both Ames and GAM are genetic reversion assays, the chemical range detected does differ to some degree between the two tests. E. coli tends to be more sensitive to chemical mutagens than Salmonella, particularly to oxidizing mutagens, cross-linking agents and hydrazines. On the other hand, Salmonella facilitates detection of aromatic amines and of nitroaromatic compounds because of substantial endogenous N-acetyl transferase metabolic activity. We selected E. coli as a host because it is a more sensitive readout for biological activity and because its DNA repair biology is better understood. In al alternative embodiment one may use Salmonella to reduce differences with Ames as much as possible.

Further Descriptions of Methods (as Described in U.S. Application No. 61/363,296)

This section may contain repetition of some methods described above but is reproduced to ensure that verbatim support is present based on the two provisional priority applications.

Technical Approach.

The detection approach is based on fusing an antibiotic resistance marker (beta-lactamase) to a fluorescent marker (GFP; FIG. 1). By fusing a fluorescent protein to the antibiotic resistance gene used as a reporter, we obtain a quantitative signal that is proportional to the number of mutation events (FIG. 2). In addition, we place our reporter in a multicopy ColE1 plasmid, increasing the number of targets (and therefore the sensitivity of the assay) by approximately two orders of magnitude (FIG. 3). Construction of an antibiotic resistance-fluorescence dual fusion protein was done as follows. As antibiotic marker we used TEM beta-lactamase, which is a standard marker of carbenicillin resistance in recombinant vectors. As a fluorescence marker we used "cycle 3" GFP, which is a mutant GFP evolved for optimal emission in E. coli (FIG. 4). As outlined in FIG. 1, the position of the antibiotic marker and that of GFP are in theory interchangeable within the reporter so long as the stop codon is placed in the N-terminal gene. Initially we fused GFP to the C-terminus of beta-lactamase (FIG. 4a). This produced robust carbenicillin resistance but no fluorescence (not shown). Next, we moved GFP to the N-terminus of beta-lactamase (FIG. 4b). This decreased transformation efficiency (suggesting poor beta-lactamase activity) and produced colonies of variable fluorescence intensity (suggesting partially impaired GFP function; FIG. 4c, 5b). Next, we replaced "cycle 3 GFP" with a superfolder GFP, which is a mutant evolved for stability in fusion constructs (J. L. Nitiss, Mol Pharmacol 50 (1996) 1095-1102). This mutant carries the same mutations of "cycle 3 GFP" plus the following additional mutations: F64L, S65T, S30R, Y39N, N105T, Y145F, I171V, and A206V. The N-terminal superfolder GFP fusion (FIG. 5a) produced both robust beta-lactamase activity as seen by the high transformation efficiency and large colony size in the presence of carbenicillin, and a strong fluorescent signal (FIG. 5c). This construct provided the dual antibiotic resistance and fluorescence protein we needed as a basis for our reversion mutagenesis assay.

Creation of Reversion Mutagenesis Reporters.

Reversion mutagenesis assays such as Ames are based on restoring a lost function caused by miscoding or truncation. In our case, inactivation needs to occur in the most N-terminal of the two genes of the fusion protein to inactivate both functions (FIG. 6). As experimental proof of concept we introduced ochre (TAA) codons at position Q69 or K209 of sfGFP. As expected, these Q69stop and K209stop constructs lost their ability to emit fluorescence but, to our surprise, retained significant levels of carbenicillin resistance, effectively precluding their use as reporters (FIG. 7). Reasoning that this ectopic expression may have been due to ribosome scanning to nearby downstream methionine residues, we introduced ochre codons in an area of sfGFP devoid of methionines: K113stop and K126stop. The presence either of these ochre codons produced significant growth lag in the presence of carbenicillin (FIG. 8a). Thus, moving the stop codons to areas devoid of methionines solved the problem. Further, there was at least a 4-order of magnitude difference in the viability of cells expressing our reporters relative to cells expressing the fusion protein (FIG. 8b) confirming that the introduction of the ochre codon had effectively suppressed functional beta-lactamase expression.

Validation of the Reversion Mutagenesis Reporters.

To establish that our reversion mutagenesis reporter can indeed detect point mutations, we introduced point mutations through expression of error-prone DNA polymerase I mutants with known mutation frequencies ranging from 1 in $10^8$ to 1 in $10^5$ nucleotides. This approach allowed controlling the mutation load while avoiding toxicity issues typically associated with the use of chemical mutagens.

Both the K113stop and K126stop reporters in cells expressing error-prone Pol I registered increased growth in the presence of carbenicillin, likely an indication of increased frequency of reversion (FIG. 8a). Colonies were fluorescent, although fluorescence was dim compared to the dual fusion protein. Intriguingly, in the absence of induced mutagenesis, cells that grew in carbenicillin were dark. Whatever the mechanism, this indicates that spontaneous mutants produce extremely low background levels of fluorescence in our assay, at least when a limited cell population (~$10^8$ cells) is tested.

We confirmed these initial findings measuring fluorescence rather than OD. In this experiment we also included a very weak mutator Pol I (I1709N; which produces mutation frequencies of only 1 mutation/$10^8$ nucleotides) to establish the sensitivity of the assay as well as the correlation between fluorescent signal and mutation frequency.

FIG. 9a presents the fluorescence readings for our positive control, which is dual fusion protein expression in culture. Expression of the highly error-prone variant of Pol I by itself causes a dramatic (>10-fold) decrease in fluorescence. This is likely due to a decrease in the copy number of the plasmid encoding the reporter (FIG. 9b). FIG. 10 presents fluorescence emission data for the two reporters, namely K113stop and K126stop. The assay registers increases in fluorescence only in samples expressing error-prone polymerases. The background of fluorescence in control samples was undetectable. The difference in fluorescence between 10,000× and 10× mutagenesis is small considering the large difference in mutation rates, but it needs to be normalized by a factor of 10 due to the difference in plasmid copy number (FIG. 9b). Thus, these preliminary data suggest that the GMA assay is very sensitive (detecting mutation frequencies as low as 1 point mutation in $10^8$) and that the fluorescent signal is proportional to the mutation load. Of the two reporters, K126stop appears to be the most promising one based on a lower background of growth (FIG. 8) and a higher intensity of fluorescent signal (FIG. 10). Using a standard gel imaging system, we were able to detect the fluorescent signal emitted by our K126stop reporter. Thus the assay may be adapted for use with gel imaging devices in the absence of fluorimeters (FIG. 11).

We confirmed that fluorescent colonies carried mutations at position K126; of three sequenced fluorescent colonies, one had reverted to wild type (TAA→AAA), the second mutated to leucine (TAA→TTA), and the third went to tyrosine (TAA→TAT). This diversity in the K126 mutations suggests that this site is tolerant to point mutations, making it a particularly convenient site for a mutagenesis reversion assay.

Discussion.

In this disclosure we present a system, 'Green fluorescence Amplification Mutation (GAM) assay, which provides a quantitative readout for mutagenesis. This method is based on a reporter plasmid bearing beta-lactamase fused to green fluorescent protein. Reversion of an inactivating mutation at the N-terminus of the fusion protein leads to both antibiotic resistance and fluorescence that can be detected by fluorimetry or by standard gel imaging systems. In the process of creating the dual function protein, we found that placing GFP at the N-terminus was critical, as well as using a "superfolder" form of GFP. When the standard "cycle 3" form of GFP was used, a wide variation in fluorescence intensities and of antibiotic resistance phenotypes was observed, suggesting impaired fluorescence and carbenicillin resistance (FIGS. 4c, 5b). Given the known tendency of GFP to misfold and to aggregate, the most parsimonious explanation is cycle3 GFP misfolding, in turn interfering with beta-lactamase activity (FIG. 4,5). Replacing cycle 3 GFP with a more stable form of GFP improved the functionality of both GFP and beta-lactamase, further supporting the notion that the original problem was due GFP misfolding. We validated the GMA assay through expression of a panel of low-fidelity DNA polymerase I mutants. DNA polymerase I initiates leader strand synthesis in our reporter plasmid, introducing mutations at a known frequency. This avoids problems of toxicity associated with the use of chemical mutagens while facilitating control of the mutation load. We established that the fluorescent signal of the assay correlates with mutation frequency (after normalization for differences in copy number) and that GMA exhibits exquisite sensitivity, detecting mutation frequencies as low as 1 in $10^8$. This frequency is only 10 times higher than the spontaneous mutation rate in E. coli.

It is somewhat surprising to find that spontaneous mutagenesis produced no significant background in our assay, since the assay itself is insensitive to the source of the mutations. It could be due to a bias in spectrum, as indels are the most frequent type of spontaneous mutation, whereas our assay detects largely point mutations. However, we do get some growth under antibiotic selection in the absence of induced mutagenesis, particularly in the case of the K113stop reporter. In this case, however, the colonies are dark (FIG. 8a,b). This may be attributable to ochre tRNA suppression or to errors in the expression of the transcript. Either or both mechanisms would allow expression of a fraction of the mRNA of our dual fusion protein, sufficient to confer some antibiotic protection but not enough to emit a detectable fluorescent signal. These effects appear to be context-dependent since the position of the ochre codon has a dramatic effect on functional expression of antibiotic resistance (FIGS. 7,8). While we clearly detect significant fluorescent signal (up to 500 RFUs), the level of signal is still 5-fold lower than that of our positive control (compare FIGS. 5c and 8b and FIGS. 9 and 10). This poor signal may result from mutations other than reversion to the original lysine AAA in the ochre (TAA) codon (FIG. 12) or from incomplete penetrance of the reversion within the multicopy plasmid population. Having recovered two additional point mutations at position 126 in fluorescent colonies suggests that this site tolerates point mutations, although more sequence is required to establish the degree of tolerance. Therefore we favor the hypothesis that the plasmids containing mutagen-induced point mutations may coexist with wild-type plasmids within the same cell, decreasing the fluorescent signal. This could be solved by increasing the concentration of carbenicillin in our selections.

In sum, here we present a mutagenesis assay that is conceptually similar to the Ames' test but that produces a quantitative rather than a binary signal. This assay is highly sensitive, detecting point mutation frequencies as low a 1 in $10^8$ with minimal background. Therefore this assay allows large savings in reagents and, more important, test sample. GMA is therefore ideally suited for situations in which sample is limiting, such as early stages of drug development or for biomonitoring of complex environmental samples. A direct comparison with the traditional Ames's test will require the generation of reporters for frameshift mutations and working out conditions for bioactivation using S9 microsomal fractions.

e) amplifying the plasmids that have mutations at the reversion site, f) measuring the level of quantitative reporter protein, wherein the level of quantitative reporter protein is quantitatively proportional to the number of mutation events at the reversion site and therefore to the mutagenic potency of the test substance.

2. A method for detecting and quantitatively measuring the mutagenic potency of a test substance, the method comprising:

a) providing a test substance, b) providing a functional fluorescence-beta-lactamase fusion construct to act as a dual reporter, wherein the dual reporter comprises an antibiotic reversion reporter and a quantitative fluorescence reporter fused together in the same open reading frame and under the control of the same promoter, wherein the dual reporter possesses a reversion site at the N-terminus of the fluorescence-beta-lactamase operons, wherein the dual reporter is cloned into a multicopy plasmid, and wherein mutations at the reversion site allow read-through of the fusion protein producing both beta-lactamase and fluorescence protein, and further wherein, in the presence of an anti-

SEQUENCE LISTING

<160> NUMBER OF SEQ ID NOS: 1

<210> SEQ ID NO 1
<211> LENGTH: 28
<212> TYPE: DNA
<213> ORGANISM: Artificial Sequence
<220> FEATURE:
<223> OTHER INFORMATION: Aequorea victoria

<400> SEQUENCE: 1
gagatcctcc aggtccagtc catgtgga                                    28

The invention claimed is:

1. A method for detecting and quantitatively measuring the mutagenic potency of a test substance, the method comprising:

a) providing a test substance, b) providing a functional quantitative reporter-antibiotic resistance fusion construct to act as a dual reporter, wherein the dual reporter comprises an antibiotic reversion reporter and a quantitative reporter fused together in the same open reading frame and under the control of the same promoter, wherein the dual reporter possesses a reversion site at the N-terminus of the quantitative reporter-antibiotic resistance operon, wherein the dual reporter is cloned into a multicopy plasmid, and wherein mutations at the reversion site allow read-through of the fusion protein producing both an antibiotic resistance protein and a quantitative reporter protein, and further wherein, in the presence of an antibiotic, the production of the antibiotic resistance protein confers a selective advantage that causes amplification of mutant plasmids, thereby raising the level of quantitative reporter protein wherein the level of quantitative reporter protein is proportional to the number of mutation events at the reversion site, c) transforming a host cell with the multicopy plasmid, d) contacting the host cell to the test substance to induce mutations at the reversion site, biotic, beta-lactamase production confers a selective advantage that causes amplification of mutant plasmids, thereby raising the level of fluorescence emitted by fluorescence protein to levels that are detectable by fluorimetry, wherein fluorescence is proportional to the number of mutation events at the reversion site, c) transforming a host cell with the multicopy plasmid, d) contacting the host cell to the test substance to induce mutations at the reversion site, e) amplifying the plasmids that have mutations at the reversion site, f) measuring the fluorescent signal, wherein the amplitude of the fluorescent signal is quantitatively proportional to the number of mutation events at the reversion site and therefore to the mutagenic potency of the test substance.

3. The method of claim 1 wherein the assay is sufficiently sensitive to detect mutation frequencies of 1 in $10^8$ nucleotides.

4. The method of claim 1 wherein the method does not use GFP as a transcriptional reporter.

5. The method of claim 1 wherein the amplitude of the quantitative reporter signal of the assay is proportional to mutation frequency after normalization for differences in copy number.

6. The method of claim 1 wherein reversion mutants are amplified in two steps: (i) the mutant plasmid becomes homoplasmic, and (ii) the reversion mutant cells grow preferentially under antibiotic selection.

7. The method of claim 1 wherein the selection antibiotic is bacteriostatic but not bacteriocidal.

8. The method of claim 2 wherein the quantitative fluorescence reporter is superfolder green fluorescent protein.

9. The method of claim 1 wherein functional expression of beta-lactamase gene is suppressed.

10. The method of claim 2 wherein the mutagenic effect can be determined as the area under the curve of fluorescence relative to that of an untreated control representing spontaneous mutations.

11. The method of claim 1 wherein the method is performed as part of high-throughput screening for DNA-targeting compounds.

12. The method of claim 1 wherein the method is performed using 96-well-format.

13. A functional fluorescence-beta-lactamase fusion construct to act as a dual quantitative reporter, wherein the dual reporter comprises an antibiotic reversion reporter and a quantitative reporter fused together in the same open reading frame and under the control of the same promoter, wherein the dual reporter possesses a reversion site at the N-terminus, wherein the dual reporter is adapted to be cloned into a multicopy plasmid, and wherein mutations at the reversion site allow read-through of the fusion protein producing both and antibiotic resistance protein and a quantitative reporter protein.

14. The dual reporter construct of claim 13 wherein the antibiotic resistance gene confers resistance against beta lactam antibiotics and the quantitative reporter protein is a fluorescence protein.

15. The dual reporter construct of claim 13 cloned into a multicopy plasmid.

16. The method of claim 1 for quantitatively measuring the mutagenic potency of a test substance, wherein the quantitative reporter may be detected by fluorometry or spectrophotometry or colorimetry.

17. The method of claim 16 for quantitatively measuring the mutagenic potency of a test substance, wherein the quantitative reporter is selected from a fluorescent, luminescent or colorimetric marker.

18. The quantitative reporter-antibiotic resistance fusion dual reporter construct of claim 13, wherein the quantitative reporter may be detected by fluorometry or spectrophotometry or colorimetry.

19. The quantitative reporter-antibiotic resistance fusion dual reporter construct of claim 18, wherein the quantitative reporter is selected from a fluorescent, luminescent or colorimetric marker.

* * * * *